United States Patent
Gumbrecht et al.

(10) Patent No.: US 9,804,146 B2
(45) Date of Patent: Oct. 31, 2017

(54) ASSEMBLY FOR NUCLEIC ACID SEQUENCING BY MEANS OF TUNNEL CURRENT ANALYSIS

(71) Applicant: SIEMENS AKTIENGESELLSCHAFT, Munich (DE)

(72) Inventors: Walter Gumbrecht, Herzogenaurach (DE); Oliver Hayden, Herzogenaurach (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 241 days.

(21) Appl. No.: 14/431,896

(22) PCT Filed: Sep. 18, 2013

(86) PCT No.: PCT/EP2013/069384
§ 371 (c)(1),
(2) Date: Mar. 27, 2015

(87) PCT Pub. No.: WO2014/048816
PCT Pub. Date: Apr. 3, 2014

(65) Prior Publication Data
US 2015/0268220 A1 Sep. 24, 2015

(30) Foreign Application Priority Data
Sep. 27, 2012 (DE) .................. 10 2012 217 603

(51) Int. Cl.
*G01N 27/453* (2006.01)
*G01N 33/487* (2006.01)
*C12Q 1/68* (2006.01)

(52) U.S. Cl.
CPC ..... *G01N 33/48721* (2013.01); *C12Q 1/6869* (2013.01); *G01N 27/453* (2013.01)

(58) Field of Classification Search
CPC ........... G01N 33/48721; G01N 27/453; C12Q 1/6869
See application file for complete search history.

(56) References Cited

U.S. PATENT DOCUMENTS

| 8,487,521 B2 | 7/2013 | Hirakawa et al. ............ 313/311 |
| 2001/0019037 A1 | 9/2001 | Zakhidov et al. |

(Continued)

FOREIGN PATENT DOCUMENTS

| CN | 101605910 | 12/2009 |
| EP | 1657539 | 5/2006 |

(Continued)

OTHER PUBLICATIONS

Aleksandar P. Ivanov et al., "DNA Tunneling Detector Embedded in a Nanopore," Nano Letters, vol. 11, No. 1, Jan. 12, 2011, pp. 279-285.

(Continued)

*Primary Examiner* — J. Christopher Ball
(74) *Attorney, Agent, or Firm* — Slayden Grubert Beard PLLC

(57) ABSTRACT

An assembly for nucleic acid sequencing by tunnel current analysis has at least two electrically conductive particles having a diameter from 1 nm to 100 nm and at least two electrically insulating particles having a diameter from 1 nm to 100 nm. The particles are in particular spherically shaped. The assembly also has at least two first electrodes for contacting the electrically conductive particles and a substrate on which the first electrodes and the particles are arranged. The four particles are arranged substantially in a planar square. The conductive particles lie diagonally oppo- (Continued)

site each other, and the insulating particles lie diagonally opposite each other. The gap between the four particles is used as a solid-state nanopore for nucleic acid sequencing.

14 Claims, 3 Drawing Sheets

(56) References Cited

U.S. PATENT DOCUMENTS

| | | |
|---|---|---|
| 2002/0190415 A1 | 12/2002 | Yang et al. |
| 2004/0152091 A1 | 8/2004 | Paulus et al. ............... 435/6.11 |
| 2006/0019259 A1 | 1/2006 | Joyce |
| 2006/0086626 A1 | 4/2006 | Joyce ........................... 205/792 |
| 2007/0023909 A1 | 2/2007 | Fork et al. |
| 2007/0125181 A1 | 6/2007 | Ofek et al. |
| 2010/0188109 A1 | 7/2010 | Edel et al. |
| 2010/0244283 A1 | 9/2010 | Tsukahara et al. |
| 2010/0323173 A1 | 12/2010 | Van Roy et al. |
| 2012/0193231 A1 | 8/2012 | Afzali-Ardakani et al. |
| 2012/0193236 A1 | 8/2012 | Peng et al. |
| 2012/0193237 A1 | 8/2012 | Afzali-Ardakani et al. |

FOREIGN PATENT DOCUMENTS

| | | | |
|---|---|---|---|
| JP | 2004519248 A | 7/2004 | ............. C12M 1/00 |
| JP | 2006119140 A | 5/2006 | ............. G01N 27/30 |
| JP | 2011119071 A | 6/2011 | ............. B01J 19/12 |
| WO | 00/15844 | 3/2000 | |
| WO | 02/074984 | 9/2002 | |
| WO | 2007/041621 | 4/2007 | |
| WO | 2008/043426 A2 | 4/2008 | |
| WO | 2008/071982 | 6/2008 | |
| WO | 2011/096936 A1 | 8/2011 | ............. F02B 33/44 |
| WO | 2011/097171 | 8/2011 | |

OTHER PUBLICATIONS

Tim Albrecht, "How to Understand and Interpret Current Flow in Nanopore/Electrode Devices," ACS NANO, vol. 5, No. 8, Aug. 23, 2011, pp. 6714-6725.
German Office Action for German Priority Patent Application No. 10 2012 217 603.9, dated Jul. 30, 2013, 5 pages.
German Search Report for German Priority Patent Application No. 10 2012 217 603.7, dated Jun. 28, 2013, 5 pages.
English language copy of International Search Report for PCT/EP2013/069384, dated Nov. 20, 2013, 3 pages.
PCT/EP2013/069384, filed Sep. 18, 2013, Walter Gumbrecht et al, Siemens AG.
DE 10 2012 217 603.9, filed Sep. 27, 2012, Walter Gumbrecht et al, Siemens AG.
Chinese Office Action dated Jan. 12, 2016 in corresponding Chinese Patent Application No. 201380050219.6.

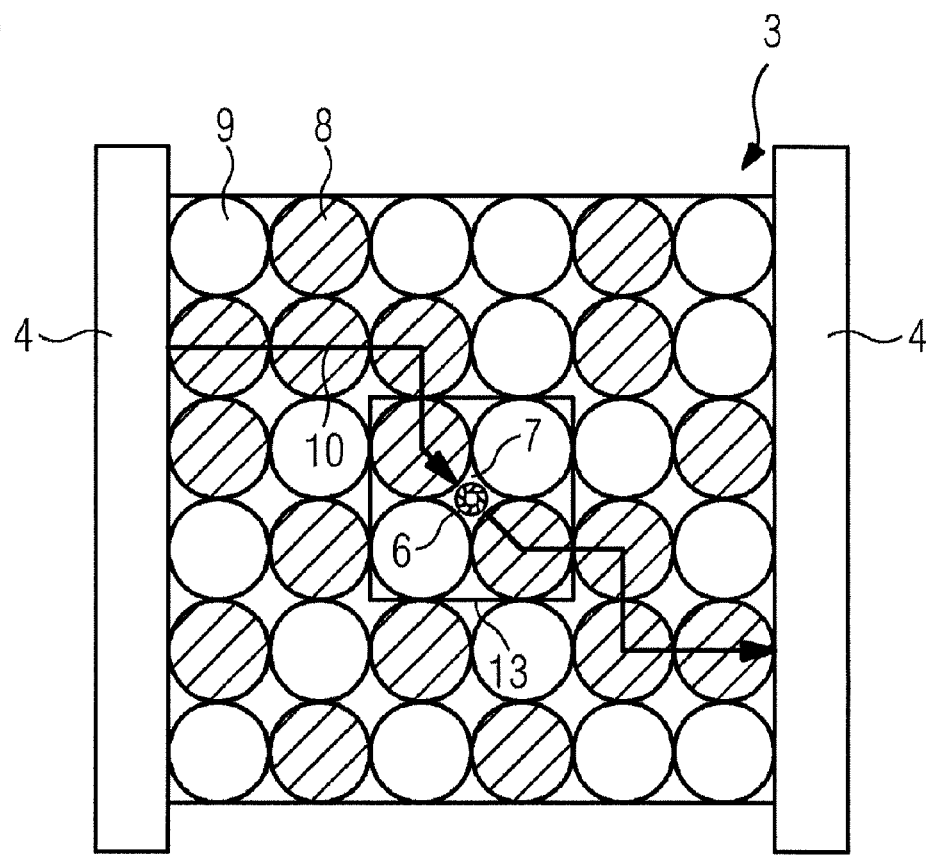

ASSEMBLY FOR NUCLEIC ACID SEQUENCING BY MEANS OF TUNNEL CURRENT ANALYSIS

CROSS REFERENCE TO RELATED APPLICATIONS

This application is based on and hereby claims priority to International Application No. PCT/EP2013/069384 filed on Sep. 18, 2013 and German Application No. 10 2012 217 603.9 filed on Sep. 27, 2012, the contents of which are hereby incorporated by reference.

BACKGROUND

The invention relates to an arrangement for nucleic acid sequencing by tunneling current analysis.

A multiplicity of methods for nucleic acid sequencing are known in the literature. They include methods of so-called sequencing-by-synthesis. In this case, a component is liberated when an appropriate nucleotide is incorporated, said component being detected by enzyme cascades. Nucleic acid sequencing in nanopores is furthermore known. It is advantageous that neither a marking of the DNA strand nor a complex reaction cascade is required in this method.

In the case of nucleic acid sequencing by nanopores, DNA strands pass through a biological or artificial (referred to as solid-state) nanopore. Individual bases of the nucleic acid strand can be analyzed as a result of a change in the pore resistance when the DNA passes through the nanopore. In this case, the DNA is passed into a conductive fluid. A voltage is applied to the fluid, with the result that an electric current flows. This current changes when different types of base (in particular guanine, cytosine, thymine, adenine) pass through the nanopore. This change is dependent on the base which passes through the pore, such that the base can be analyzed.

Alternatively, it is possible to measure a tunneling current via the pore (referred to as: sequencing-by-tunneling), wherein the tunneling current is dependent on the base situated in the pore. Tunneling current methods advantageously have a better base resolution in comparison with the measurement of the pore resistance. The latter stems from high electric field strengths within the nanopore.

These measurements are greatly dependent on the size and shape of the nanopore. Furthermore, the electrodes for applying a voltage to the nanopore have to be arranged exactly, in order to detect the tunneling current sufficiently accurately. In order to achieve a high analysis reliability of the nucleic acid sequencing by tunneling current analysis, it is desirable to produce customized nanopores with electrodes for defined applications. Most production methods for producing solid-state nanopores are based on the removal of material from a thin membrane, in a manner similar to the drilling of holes. This production is carried out in particular by electron beam-based photolithography.

It is disadvantageous that the previous arrangements of solid-state nanopores with electrodes are very complex and time-consuming to produce. A sufficiently precise arrangement of the nanopore with respect to the electrodes or a capacitor in such a way that tunneling currents can be measured with high accuracy is virtually impossible to realize technically at the present time and the production thereof is disadvantageously associated with high expenditure in terms of labor and time.

SUMMARY

One possible object is to specify an arrangement for analyzing nucleic acid sequences and a method for producing the arrangement which overcome the disadvantages mentioned.

The inventors propose an arrangement for nucleic acid sequencing by tunneling current analysis comprises. The arrangement has at least two electrically conductive particles having a diameter of 1 nm to 100 nm, in particular having a diameter of 1 nm to 10 nm. Furthermore, it comprises at least two electrically insulating particles having a diameter of 1 nm to 100 nm, in particular of 1 nm to 10 nm. The arrangement furthermore comprises at least two first electrodes for contacting the electrically conductive particles. The first electrodes and the particles are situated on a substrate. According to the proposals, the at least four particles are arranged in a substantially square planar fashion, wherein the conductive particles and insulating particles in each case lie diagonally opposite one another. A gap advantageously forms in the center of the four particles arranged in a square planar fashion. The size of said gap is in the range of nm depending on the size and shape of the particles. The gap constitutes a solid-state nanopore in the analysis of nucleic acid sequences. The arrangement makes it possible to present a defined customized nanopore.

The inventors also propose a method for producing an arrangement for nucleic acid sequencing by tunneling current analysis, depressions are produced in a substrate. At least two electrically conductive particles and at least two electrically insulating particles are introduced, in particular filled, into the depressions, wherein the particles are statistically distributed in the depressions.

In one advantageous configuration and development, the first electrodes are in each case in direct electrical contact with at least one electrically conductive particle. Advantageously, a current can thus flow through the electrically conductive particles. The arrangement of the first electrodes is advantageously such that the conductive particles form the capacitor at which a tunneling current can be measured for the analysis if a DNA or RNA strand is situated in the nanopore. The arrangement of the nanopore with respect to the capacitor is then advantageously such that tunneling currents can be measured with high accuracy, since nanopore and capacitor lie locally very closely against one another. Ideally, the capacitor gap that forms and the nanopore are identical.

In a further advantageous configuration and development, the arrangement comprises at least two second electrodes arranged orthogonally with respect to the first electrodes. These electrodes advantageously serve for the targeted movement of a DNA strand through the particles. In particular, electrodes used in gel electrophoresis in order to move the DNA/RNA through the gel are suitable for this purpose.

In a further advantageous configuration and development, the substrate comprises depressions arranged in a grid. The diameter of the depression is between 10 nm and 1 μm, in particular. The depressions advantageously constitute a fixing unit for the particles.

In a further advantageous configuration and development, the substrate is a CMOS chip. The latter is constructed in layers, wherein insulating and conductive layers are arranged one above another. The CMOS chip typically already comprises a device for supplying the electrodes with voltage and for measuring a current between the first electrodes.

In a further advantageous configuration and development, the particles are spherical particles. Spherical particles advantageously arrange themselves in a sphere packing. The diameters of the resulting gaps can advantageously be calculated. Customized nanopores for nucleic acid sequencing can thus be formed.

In a further advantageous configuration and development, the electrically conductive particles comprise gold.

The electrically conductive particles typically have substantially the same size. The sphere packing is advantageously regular as a result. In a further advantageous configuration and development, the electrically insulating particles comprise polystyrene.

In a further advantageous configuration and development, the electrically conductive particles are fixedly connected to one another. This fixed connection can advantageously be produced with the aid of a plating process. Alternatively, this fixed connection can be effected by an electrically conductive coating produced in particular with the aid of the electroless deposition of metal. The electrical contact between the electrically conductive particles which are in each case at a distance from one another of less than 1 nm is thus advantageously ensured.

In a further advantageous configuration and development, the depressions are filled with at least 100 electrically conductive and electrically insulating particles.

In a further advantageous configuration and development, the depressions already filled with electrically conductive and electrically insulating particles are selected which have exactly an arrangement as proposed, that is to say with a nanopore. The tunneling current which flows when a DNA/RNA passes through the nanopore is advantageously measured without the superposition of further tunneling currents.

In a further advantageous configuration and development, the electrically conductive particles which are at a distance from one another of less than 1 nm are coated with an electrically conductive layer in such a way that they are in electrical contact with one another. The electrical contact between the electrically conductive particles which are in each case at a distance from one another of less than 1 nm is thus advantageously ensured.

In a further advantageous configuration and development, the electrically conductive particles are coated by electroless deposition of metal.

BRIEF DESCRIPTION OF THE DRAWINGS

These and other objects and advantages of the present invention will become more apparent and more readily appreciated from the following description of the preferred embodiments, taken in conjunction with the accompanying drawings of which:

FIG. 3 schematically shows a depression 3 with two first electrodes 4 in a plan view from above with an electric current 10.

DETAILED DESCRIPTION OF THE PREFERRED EMBODIMENT

Figure 1:
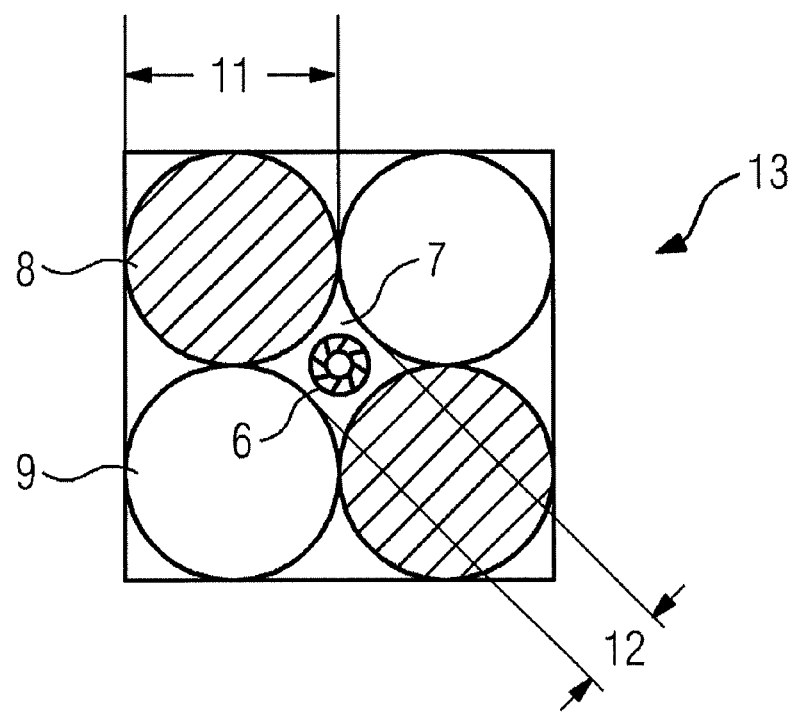
FIG. 1 schematically shows a particle arrangement 13 in a plan view from above.

Reference will now be made in detail to the preferred embodiments of the present invention, examples of which are illustrated in the accompanying drawings, wherein like reference numerals refer to like elements throughout.

The particle arrangement 13 illustrated schematically in FIG. 1 comprises two conductive particles 8, two insulating particles 9, and DNA 6. The particles are illustrated in the section in a plan view from above, that is to say that the round areas illustrated show the sectional area of a particle with the maximum diameter thereof. The helical DNA 6 can also be seen from above.

The conductive particles 8 are formed of gold. The insulating particles 9 are formed of polystyrene. Alternatively, the insulating particles 9 are formed of latex. The diameter 11 of the particles 8 and 9 is 5 nm. The gap that forms between the particles constitutes an active nanopore 7 for a DNA sequencing. It has a pore diameter 12 of 2 nm.

Figure 2:
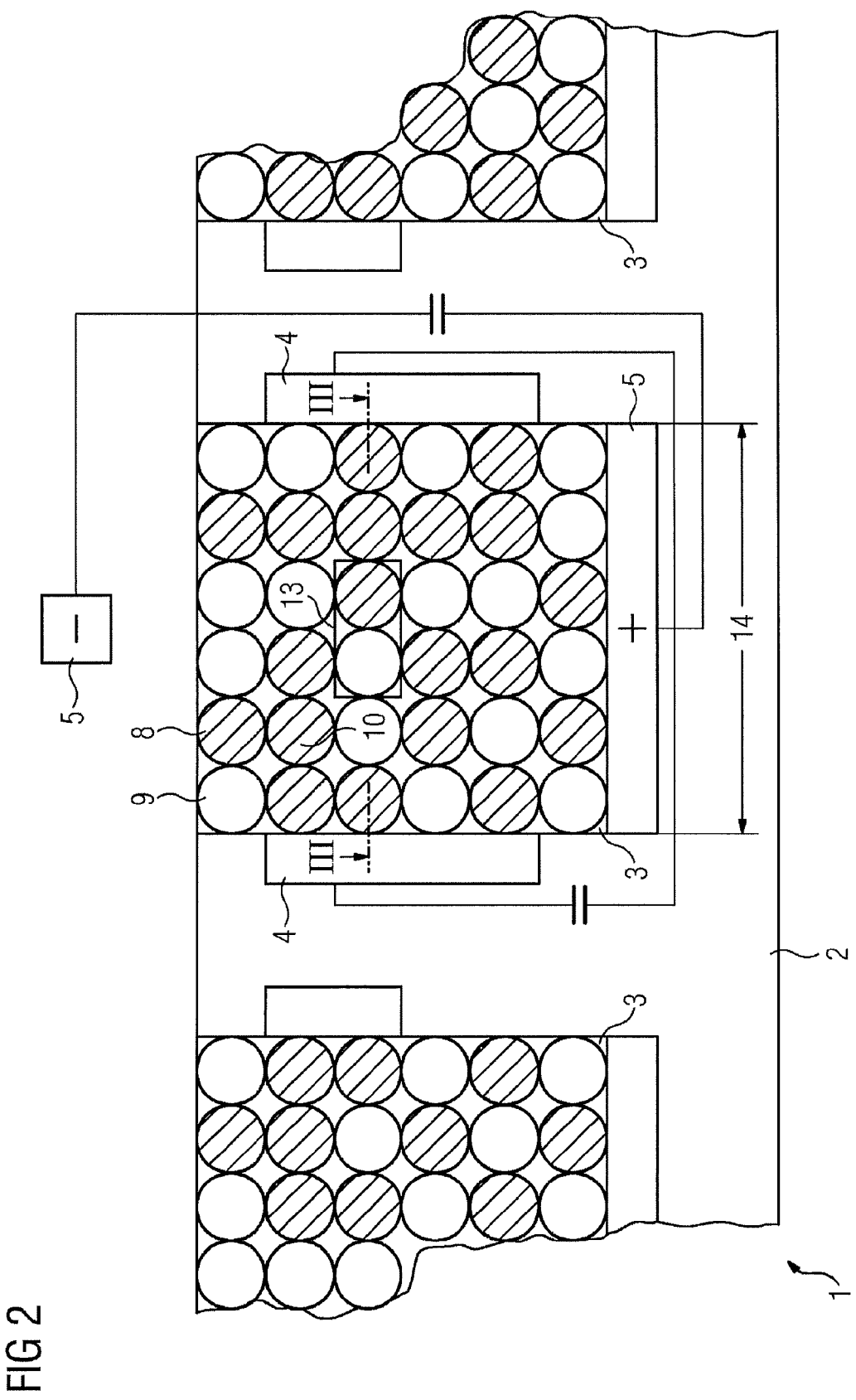
FIG. 2 schematically shows the construction of the grid arrangement 1 from the side. The grid arrangement 1 comprises the particle arrangement 13.

FIG. 2 shows a side view of the grid arrangement 1 with for example three depressions 3. The substrate 2 comprises silicon, in particular. The depression diameter 14 is typically 30-150 nm. The depression diameter 14 in this exemplary embodiment is 35 nm. A respective first electrode 4 is situated on two of the lateral walls of the depression 3. The first electrodes 4 are expediently supplied with voltage. The first electrodes 4 can extend over parts of the lateral walls, as in this example. Alternatively, the first electrodes 4 can also extend over the entire area of the lateral walls. A respective second electrode 5 is arranged at the bottom of the depression 3 and above the substrate 2. The voltage supply of the electrodes 4 and 5 is illustrated by way of example on the basis of the middle depression 3 in FIG. 2.

The substrate is typically a CMOS chip. The depressions are arranged in a grid on said CMOS chip. One of the second electrodes 5 and both the first electrodes 4 are applied on said substrate, i.e. the CMOS chip. The CMOS chip has very good analog-electronic properties that ensure a precise measurement of the tunneling current. By an analog-to-digital conversion and a fast multiplexing method, in particular, it is possible to read a multiplicity of electrodes for measuring the tunneling current. The electrodes are contacted in particular by the topmost metalization plane of the CMOS chip.

The depressions 3 are introduced into silicon oxide or silicon nitride by an etching technique.

The depression 3 is filled with a mixture of conductive particles 8 and insulating particles 9, wherein the composition of the mixture is divided substantially in equal halves and the particles are distributed statistically in the depression.

The second electrodes 5 are supplied with voltage, such that the DNA 6 is transported into the depression 3, in a manner similar to the transport of DNA in an electrophoresis arrangement.

FIG. 3 illustrates a section through one of the depressions 3. A DNA 6 is situated in the active nanopore 7. If voltage is applied to the first electrodes 4, then an electric current 10 arises in the particle arrangement 13. A tunneling current flows between the conductive particles 8, wherein the conductive particles 8 themselves constitute the capacitors. The tunneling current is dependent on the base of the DNA 6 which passes through the active nanopore 7. With the aid of a measurement of the tunneling current between the two first electrodes 4, it is thus possible to analyze the base in the active nanopore 7.

The conductive particles 8 directly adjoining the active nanopore 7 advantageously form the capacitor, which enables a shorter pore length. This significantly improves the base resolution of the DNA sequencing.

The current between the second electrodes 5 moves the DNA 6 through the active nanopore 7, such that one base after another passes through the active nanopore 7 and the nucleic acid sequence is analyzed. The second electrodes 5 are not supplied with voltage during the measurement of the tunneling current. Alternatively, a constant voltage supply of the second electrodes 5 can be effected if it does not disturb the measurement of the tunneling current.

In order to address suitable systems, in particular particle arrangements 13, with active nanopores 7, the depressions 3 are firstly filled with an electrolyte solution. Afterwards, an AC voltage is applied to the depression 3 filled with particles and electrolyte solution and the resistance is measured. The resistance is characteristic of the arrangement of the non-conductive and conductive particles 8 and 9.

If a depression 3 comprises a plurality of particle arrangements 13 in which DNA 6 is simultaneously situated, then this leads to a plurality of tunneling currents in one depression 3. These tunneling currents then cannot be discriminated, and so this depression 3 cannot be evaluated. A grid comprises 1000 depressions 3 in this example, however, such that nevertheless enough depressions 3 with exactly one particle arrangement 13 are available for the DNA analysis.

Plating can be carried out for fixing the particles. The conductive particles 8 composed of gold are connected to one another by so-called electroless plating. Alternatively, this contacting can take place in a genuinely electrolytic fashion. The conductive particles are thus fixed and an electrical contact between the conductive particles 8 directly touching one another is ensured.

As an alternative to DNA sequences, RNA sequences can also be analyzed. The sequence analysis of short RNA fragments, in particular of miRNAs (micro-RNAs) or mRNAs (messenger RNA), is also possible.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV*, 69 USPQ2d 1865 (Fed. Cir. 2004).

The invention claimed is:

1. An arrangement, comprising:
    a plurality of electrically conductive particles, each electrically conductive particle having a diameter of 1 nm to 100 nm;
    a plurality of electrically insulating particles, each electrically insulating particle having a diameter of 1 nm to 100 nm;
    at least two first electrodes contacting the electrically conductive particles;
    a substrate on which the at least two first electrodes, the plurality of electrically conductive particles, and the plurality of electrically insulating particles are arranged,
    the plurality of electrically conductive particles and the plurality of electrically insulating particles being arranged on the substrate in a substantially square planar fashion such that at least two of the electrically conductive particles lie diagonally opposite one another and such that at least two of the electrically insulating particles lie diagonally opposite to one another,
    the at least two electrically conductive particles being electrically insulated from one another by a gap;
    wherein the substrate includes depressions arranged in a grid.

2. The arrangement as claimed in claim 1, wherein each of the at least two first electrodes is in direct electrical contact with at least one of the electrically conductive particles.

3. The arrangement as claimed in claim 1, further comprising at least two second electrodes arranged orthogonally with respect to the at least two first electrodes.

4. The arrangement as claimed in claim 1, wherein the substrate is a CMOS chip.

5. An arrangement, comprising:
    a plurality of electrically conductive particles, each electrically conductive particle having a diameter of 1 nm to 100 nm;
    a plurality of electrically insulating particles, each electrically insulating particle having a diameter of 1 nm to 100 nm;
    at least two first electrodes contacting the electrically conductive particles;
    a substrate on which the at least two first electrodes, the plurality of electrically conductive particles, and the plurality of electrically insulating particles are arranged,
    the plurality of electrically conductive particles and the plurality of electrically insulating particles being arranged on the substrate in a substantially square planar fashion such that at least two of the electrically conductive particles lie diagonally opposite one another and such that at least two of the electrically insulating particles lie diagonally opposite to one another,
    the at least two electrically conductive particles being electrically insulated from one another by a gap;
    wherein each of electrically conductive particles and each of the electrically insulating particles is a spherical particle.

6. The arrangement as claimed in claim 1, wherein each of the electrically conductive particles is formed of gold.

7. The arrangement as claimed in claim 1, wherein each of the electrically conductive particles has substantially a same size.

8. An arrangement, comprising:
    a plurality of electrically conductive particles, each electrically conductive particle having a diameter of 1 nm to 100 nm;
    a plurality of electrically insulating particles, each electrically insulating particle having a diameter of 1 nm to 100 nm;
    at least two first electrodes contacting the electrically conductive particles;
    a substrate on which the at least two first electrodes, the plurality of electrically conductive particles, and the plurality of electrically insulating particles are arranged,
    the plurality of electrically conductive particles and the plurality of electrically insulating particles being arranged on the substrate in a substantially square planar fashion such that at least two of the electrically conductive particles lie diagonally opposite one another and such that at least two of the electrically insulating particles lie diagonally opposite to one another,
    the at least two electrically conductive particles being electrically insulated from one another by a gap;
    wherein each of the electrically insulating particles is formed of polystyrene.

9. An arrangement, comprising:
a plurality of electrically conductive particles, each electrically conductive particle having a diameter of 1 nm to 100 nm;
a plurality of electrically insulating particles, each electrically insulating particle having a diameter of 1 nm to 100 nm;
at least two first electrodes contacting the electrically conductive particles;
a substrate on which the at least two first electrodes, the plurality of electrically conductive particles, and the plurality of electrically insulating particles are arranged,
the plurality of electrically conductive particles and the plurality of electrically insulating particles being arranged on the substrate in a substantially square planar fashion such that at least two of the electrically conductive particles lie diagonally opposite one another and such that at least two of the electrically insulating particles lie diagonally opposite to one another,
the at least two electrically conductive particles being electrically insulated from one another by a gap;
wherein the electrically conductive particles that are at a distance from one another of less than 1 nm with respect to one another are fixedly connected to one another.

10. A method for producing an arrangement, comprising:
producing a plurality of depressions in a substrate;
filling each of the depressions with a plurality of electrically conductive particles and a plurality of electrically insulating particles,
the electrically conductive particles and the electrically insulating particles being statistically distributed in each of the depressions such that at least two of the electrically conductive particles lie diagonally opposite one another and such that at least of the electrically insulating particles lie diagonally opposite to one another, the at least two electrically conductive particles being electrically insulated from one another by a gap; and
applying at least two electrodes on the substrate for each of the depressions, the at least two electrodes contacting the electrically conductive particles in the respective depression.

11. The method as claimed in claim 10, wherein each of the depressions is filled with at least 100 particles including the plurality of electrically conductive particles and the plurality of electrically insulating particles.

12. The method as claimed in claim 10, wherein the depressions are produced on the substrate in a grid.

13. The method as claimed in claim 10, wherein the electrically conductive particles that are at a distance from one another of less than 1 nm are coated with an electrically conductive layer in such a way that they are in electrical contact with one another.

14. The method as claimed in claim 13, wherein the electrically conductive particles are coated by electroless deposition of metal.

* * * * *